(12) United States Patent
Shigemoto et al.

(10) Patent No.: US 7,993,589 B1
(45) Date of Patent: Aug. 9, 2011

(54) AIR-CONDITIONING APPARATUS

(75) Inventors: Naoyuki Shigemoto, Osaka (JP); Jun Katayama, Yao (JP)

(73) Assignee: Sharp Kabushiki Kaisha, Osaka (JP)

( * ) Notice: Subject to any disclaimer, the term of this patent is extended or adjusted under 35 U.S.C. 154(b) by 215 days.

(21) Appl. No.: 11/996,278

(22) PCT Filed: Jul. 20, 2006

(86) PCT No.: PCT/JP2006/314362
§ 371 (c)(1),
(2), (4) Date: Jan. 18, 2008

(87) PCT Pub. No.: WO2007/010972
PCT Pub. Date: Jan. 25, 2007

(30) Foreign Application Priority Data

Jul. 22, 2005 (JP) .................... 2005-213283

(51) Int. Cl.
*A62B 7/08* (2006.01)
*B01D 39/14* (2006.01)

(52) U.S. Cl. .......................... 422/122; 55/524

(58) Field of Classification Search .................. 422/122; 55/DIG. 12, 524, 52
See application file for complete search history.

(56) References Cited

FOREIGN PATENT DOCUMENTS

| JP | 04004011 A | * | 1/1992 |
|---|---|---|---|
| JP | 4-288163 A | | 10/1992 |
| JP | 09-239229 A | | 9/1997 |
| JP | 09271616 A | * | 10/1997 |
| JP | 10-235129 A | | 9/1998 |
| JP | 11-114333 A | | 4/1999 |
| JP | 2000314393 A | * | 11/2000 |
| JP | 2002-058729 A | | 2/2002 |
| JP | 2002-119809 A | | 4/2002 |
| JP | 2003-210559 A | | 7/2003 |
| JP | 2004-255159 A | | 9/2004 |

* cited by examiner

*Primary Examiner* — Kevin C Joyner
(74) *Attorney, Agent, or Firm* — Birch, Stewart, Kolasch & Birch, LLP

(57) ABSTRACT

There are provided a sirocco fan (130) and a filter unit (251). Filter unit (251) includes a deodorization filter (252), a filter (253) for removing an organic matter containing an aldehyde group, and an antibacterial/dust filter (254). Deodorization filter (252) contains a carbon monoxide removing catalyst.

8 Claims, 23 Drawing Sheets

AIR-CONDITIONING APPARATUS

TECHNICAL FIELD

The present invention relates to air conditioning apparatuses, such as an air conditioning apparatus including a filter having a carbon monoxide removing catalyst or a formaldehyde removing filter.

BACKGROUND ART

There are known air conditioning apparatuses as apparatuses for controlling temperature, humidity, or a degree of pollution of air in a room. In the air conditioning apparatuses, the air in the room is taken into an inside of the apparatus, a physical property of the air taken in the apparatus is changed into a desired state, and the air is blown to an outside of the apparatus. Particularly, the air conditioning apparatus having an air cleaning function for improving the degree of pollution of the air in the room receives attention with a recent change in living environments.

Conventionally air cleaners having a dust trapping function and a deodorization function have been widespread. Furthermore, in addition to these functions, air cleaners having an antibacterial or bacteria elimination function against physically-harmful airborne bacteria are becoming common in recent years. As used herein, the "antibacterial function" shall mean that growth of the bacteria adhering to a fibrous filter is suppressed, and the "bacteria elimination function" shall mean that microorganisms are killed to decrease an absolute number thereof.

In such air cleaners, the dust trapping function, the deodorization function, and the antibacterial function are exerted by various filters disposed in an air flow path. Generally, the air cleaner includes a duct filter having the dust trapping function and a deodorization filter having the deodorization function as the various filters. The trapping filter traps the dust in the air. The deodorization filter traps and decomposes an odor component in the air. The bacterial filter controls or eliminates the physically-harmful airborne bacteria.

For example, Japanese Patent Laying-Open No. 11-114333 (Patent Document 1) discloses a deodorization filter including a powder activated carbon deodorization portion and a granular activated carbon deodorization portion. Japanese Patent Laying-Open No. 9-239229 (Patent Document 2) discloses a humidity conditioning tool containing wood charcoal and zeolite. Japanese Patent Laying-Open No. 2002-58729 (Patent Document 3) discloses a deodorization filter including an activated carbon layer and a nonwoven layer.

Recently, awareness of an indoor environment is increasingly raised. Even in the air cleaner, a function of decomposing and removing a physically-harmful substance is demanded in addition to the dust trapping function, the deodorization function, and the antibacterial function. Examples of the physically-harmful substance include a VOC gas (Volatile Organic Compound) such as toluene and formaldehyde and carbon monoxide contained in cigarette smoke.

As to a filter having the function of decomposing and removing the physically-harmful substance, for example, Japanese Patent Laying-Open No. 10-235129 (Patent Document 4) discloses a filter containing an aldehyde removing chemical agent, a nitrogen-system substance removing chemical agent, and a sulfur-system chemical agent.

Patent Document 1: Japanese Patent Laying-Open No. 11-114333

Patent Document 2: Japanese Patent Laying-Open No. 9-239229

Patent Document 3: Japanese Patent Laying-Open No. 2002-58729

Patent Document 4: Japanese Patent Laying-Open No. 10-235129

DISCLOSURE OF THE INVENTION

Problems to be Solved by the Invention

However, in order to decompose and remove the carbon monoxide, it is necessary that the air containing the carbon monoxide be heated to a high temperature and caused to pass through a catalyst layer for being able to decompose and remove the carbon monoxide. In order to decompose and remove the carbon monoxide, an air flow path including the catalyst layer is formed by a heat-resistant material, and a space is required to dispose the device for generating the high temperature and the catalyst layer. However, it is difficult that a small home appliance such as a home air-cleaner include the function of generating the high temperature. Therefore, in Patent Documents 1 to 4, it is difficult to include the function of decomposing and removing the carbon monoxide.

Although the filter disclosed in Patent Document 4 contains the aldehyde removing chemical agent, a bearing member bearing the aldehyde removing chemical agent mixed in the nitrogen-system substance removing chemical agent is used due to restriction of the space. Therefore, it is difficult to form the filter for removing only the aldehyde.

In view of the foregoing, an object of the present invention is to provide an air conditioning apparatus having the carbon monoxide removing function. Another object of the present invention is to provide an air conditioning apparatus including the filter only for removing the organic matter having the aldehyde group.

Means for Solving the Problems

In accordance with a first aspect of the present invention, an air conditioning apparatus includes a blowing fan and a filter unit, wherein the filter unit includes a filter containing a carbon monoxide removing catalyst.

In the air conditioning apparatus according to the first aspect of the present invention, the carbon monoxide removing catalyst promotes reaction of the carbon monoxide in the air into the carbon dioxide, so that the carbon monoxide in the air can be removed.

The filter unit contains the catalyst capable of removing the carbon monoxide at room temperature, whereby a space for a device heating the air to a high temperature is not required. Therefore, the air conditioning apparatus having the carbon monoxide removing function can be miniaturized.

The "carbon monoxide removing catalyst" may include a function of removing another substance as long as the carbon monoxide removing catalyst has the function of being able to remove the carbon monoxide.

In the above air conditioning apparatus, preferably the filter unit further includes one organic matter removing filter for removing an organic matter containing an aldehyde group.

Therefore, the carbon monoxide and the organic matter containing the aldehyde group can be removed in the air. The filter unit includes the one organic matter removing filter, so that the organic matter containing the aldehyde group can effectively be removed.

Examples of the organic matter containing the aldehyde group include formaldehyde, acetaldehyde, and propylene aldehyde. It is preferable that particularly the formaldehyde be removed as the organic matter containing the aldehyde group. This is because the formaldehyde causes a sick house syndrome.

The "organic matter removing filter" may include a function of removing another substance as long as the organic matter removing filter has the function of being able to remove the organic matter containing the aldehyde group.

In the above air conditioning apparatus, the organic matter removing filter is preferably disposed on a downwind side of the filter containing the catalyst.

In the filter unit, the filter containing the catalyst also acts as a prefilter for trapping large dust in the air sucked by the fan. Therefore, the organic matter removing filter can more effectively remove the organic matter.

In the above air conditioning apparatus, preferably the filter unit further includes a deodorant for removing an odor component. Therefore, the odor component in the air can also be removed.

In the above air conditioning apparatus, the catalyst and the deodorant are preferably contained in one filter. Accordingly, the carbon monoxide and the odor component are removed by the one filter, so that the filter unit can be thinned.

In the above air conditioning apparatus, the one filter preferably contains the catalyst in one of a relatively upper portion and a relatively lower portion, and the deodorant in other portions. Therefore, the filter unit can be thinned.

In the above air conditioning apparatus, the one filter preferably contains the deodorant and the catalyst while the catalyst is mixed in the deodorant. Therefore, the filter unit can be thinned.

In the above air conditioning apparatus, the one filter preferably includes a plurality of coupled deodorant storage chambers for storing the deodorant and a plurality of coupled catalyst storage chambers for storing the catalyst, while the deodorant storage chambers and the catalyst storage chambers are alternately disposed with each other. Therefore, the filter unit can be thinned.

In the above air conditioning apparatus, preferably the filter unit further includes one organic matter removing filter for removing an organic matter containing an aldehyde group.

Therefore, the carbon monoxide and the organic matter containing the aldehyde group can be removed in the air. The filter unit includes the one organic matter removing filter, so that the organic matter containing the aldehyde group can effectively be removed. In a case where only the function of the organic matter removing filter is decreased, convenience is enhanced because only the organic matter removing filter can be replaced without replacing other members.

In the above air conditioning apparatus, preferably the organic matter removing filter is disposed on a downwind side of the one filter.

In the filter unit, the filter containing the catalyst also acts as the prefilter for trapping the large dust in the air sucked by the fan. Therefore, the organic matter removing filter can more effectively remove the organic matter.

In the above air conditioning apparatus, the filter unit preferably includes one catalyst filter containing the catalyst and one deodorization filter containing the deodorant.

The "deodorization filter" may include a function of removing another substance as long as the deodorization filter has the function of being able to remove the odor component.

Therefore, because the large amounts of catalyst and deodorant can be contained, the large amounts of carbon monoxide and odor component can be removed in the air. Additionally, the convenience is enhanced because only the catalyst filter or deodorization filter whose function is decreased can easily be replaced.

In the above air conditioning apparatus, preferably the catalyst filter includes a plurality of coupled catalyst storage chambers for storing the catalyst, the deodorization filter includes a plurality of coupled deodorant storage chambers for storing the deodorant, while a coupling portion of the deodorant storage chambers is disposed to overlap a substantial center portion of the catalyst storage chamber.

Therefore, the space portions of the catalyst storage chamber and deodorant storage chamber do not overlap with each other, so that the filter unit can be thinned.

In the above air conditioning apparatus, the catalyst filter is preferably disposed on a downwind side of the deodorization filter.

The deodorization filter can trap the dust larger than that trapped by the catalyst filter. Therefore, the catalyst filter is disposed on the windward side to allow the carbon monoxide and the odor component to be more effectively removed.

In the above air conditioning apparatus, preferably the filter unit further includes one organic matter removing filter for removing an organic matter containing an aldehyde group.

Therefore, the carbon monoxide and the organic matter containing the aldehyde group in the air can be removed. The filter unit includes the one organic matter removing filter, so that the organic matter containing the aldehyde group can effectively be removed.

In the above air conditioning apparatus, the organic matter removing filter is preferably disposed on a downwind side of the catalyst filter.

In the filter unit, at least one of the catalyst filter and the deodorization filter also acts as the prefilter for trapping the large dust in the air sucked by the fan. Therefore, the organic matter removing filter can more effectively remove the organic matter.

In accordance with a second aspect of the present invention, an air conditioning apparatus includes a blowing fan and a filter unit, wherein the filter unit includes one deodorization filter for removing an odor component; and one organic matter removing filter for removing an organic matter containing an aldehyde group. In the air conditioning apparatus according to the second aspect of the present invention, the odor component and the organic matter containing the aldehyde group in the air can be removed. The filter unit includes the one organic matter removing filter, so that the organic matter containing the aldehyde group can effectively be removed.

In a case where only the function of the organic matter removing filter is decreased, only the organic matter removing filter can be replaced without replacing other members. Therefore, the convenience is enhanced because the filter can be replaced according to a use environment of the air conditioning apparatus.

In the above air conditioning apparatus, the organic matter removing filter is preferably disposed on a downwind side of the catalyst filter.

In the filter unit, the deodorization filter also acts as the prefilter for trapping the large dust in the air sucked by the fan. Therefore, the organic matter removing filter can more effectively remove the organic matter.

Effects of the Invention

In the air conditioning apparatus having the above-described configuration, the carbon monoxide removing catalyst promotes the reaction of the carbon monoxide in the air into the carbon dioxide, so that the carbon monoxide in the air can be removed. Additionally, the odor component and the organic matter containing the aldehyde group can effectively be removed in the air by the one deodorization filter and the one organic matter removing filter.

DESCRIPTION OF THE REFERENCE SIGNS 00, 200, and 300 air cleaner, 110 main body casing, 112 foot portion, 114 handgrip portion, 116 upper panel portion, 118 recess portion. 120 partition wall, 121 communication hole, 122 metal guard, 123 flow path forming member, 124 inlet port, 126A and 126B air outlet, 126a and 126b louver, 130 sirocco fan, 132 motor, 134 ion generator, 136 dust sensor, 138 odor sensor, 140 front panel, 141 side portion, 150 filter pressing frame, 150a frame body, 150b cut-in portion, 150c hook portion, 150d insertion portion, 151, 251, and 351 filter unit, 152, 252, 256, and 352 deodorization filter, 152A filter attaching belt, 153, 253, and 353 organic matter removing filter, 154, 254, and 354 antibacterial/dust filter, 160 power button, 161 ion generator switching button, 162 running mode switching button, 163 shortcut button, 171 ion generator operating state display lamp, 172 running mode display lamp, 173 shortcut operation display lamp, 174 pollution state display unit, 174a light emitting diode, 175 ion generator operating state display unit, 175a light emitting diode, 190 power cord, 252a catalyst, 252b deodorant, 252c bag, 252d spacer, 252e another frame material, 255 catalyst filter, S1 front space, S2 rear space

BEST MODES FOR CARRYING OUT THE INVENTION

Preferred embodiments of the present invention will be described in detail with reference to the drawings. In the following embodiments, a floor-mounted air cleaner having the air cleaning function is described as the air conditioning apparatus by way of example.

First Embodiment

Figure 1:
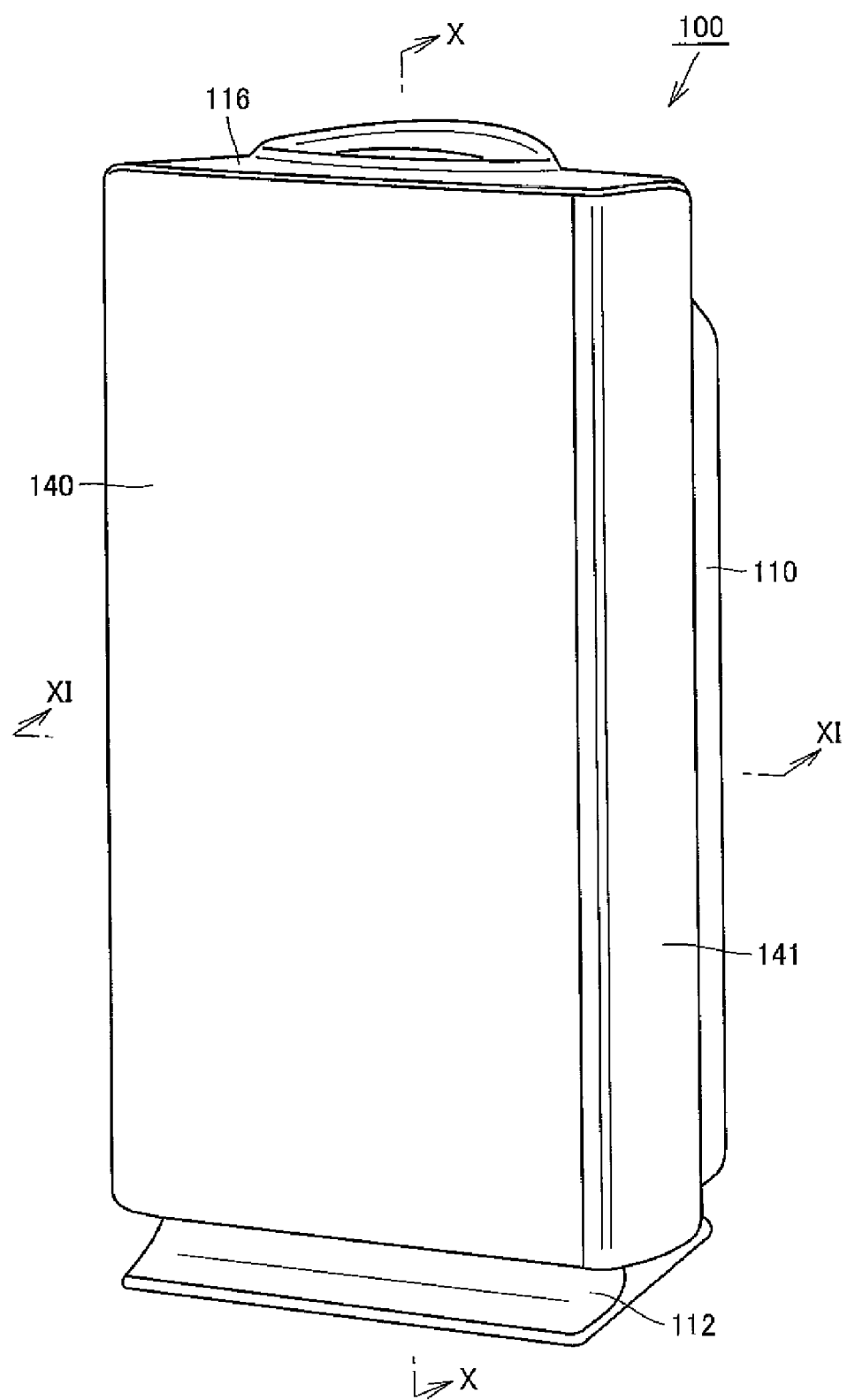
FIG. 1 is a schematic perspective view of an air cleaner according to a first embodiment of the present invention when viewed from a front face side.
Figure 2:
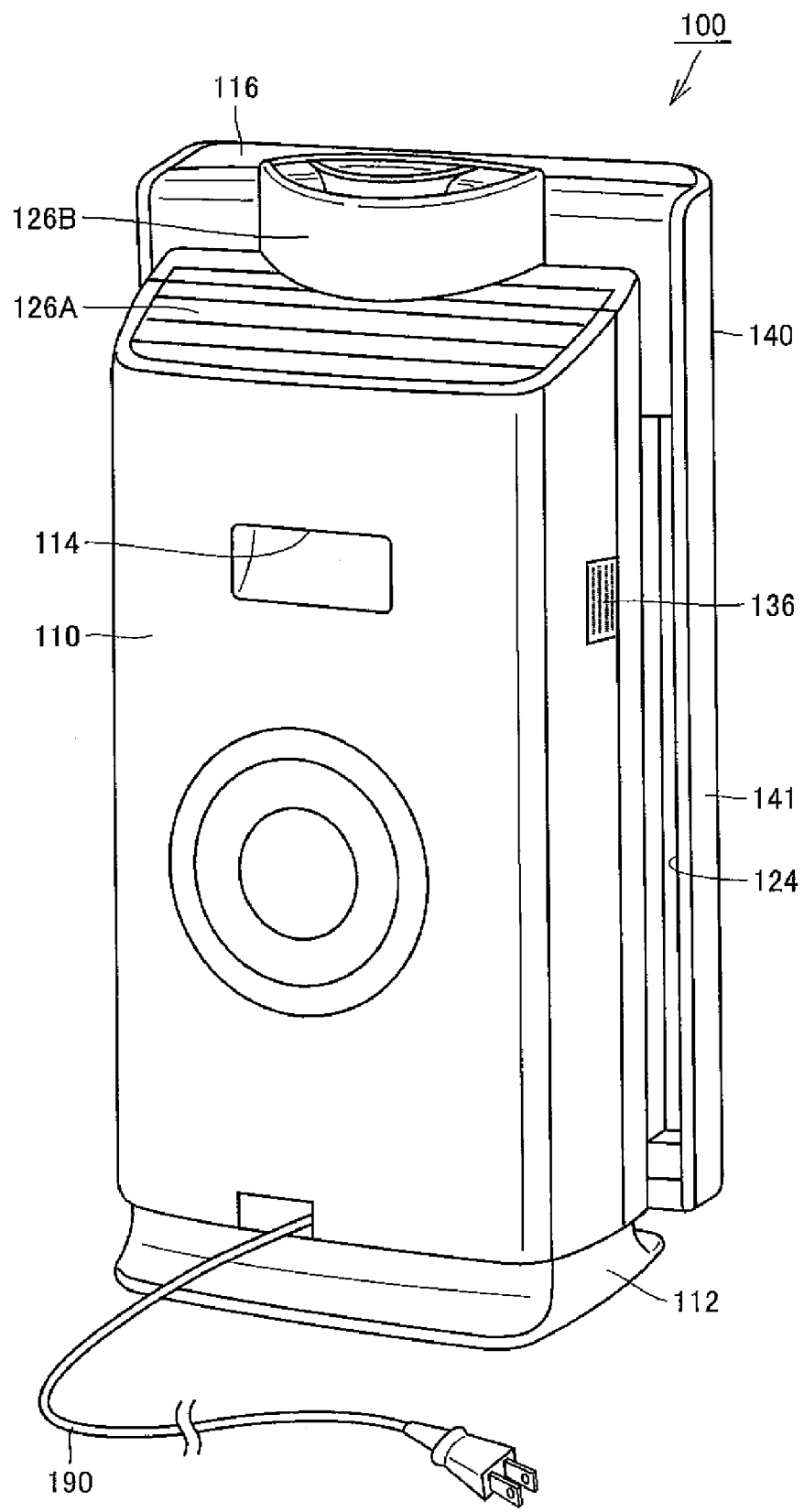
FIG. 2 is a schematic perspective view of the air cleaner according to the first embodiment of the present invention when viewed from a rear face side.
Figure 3:
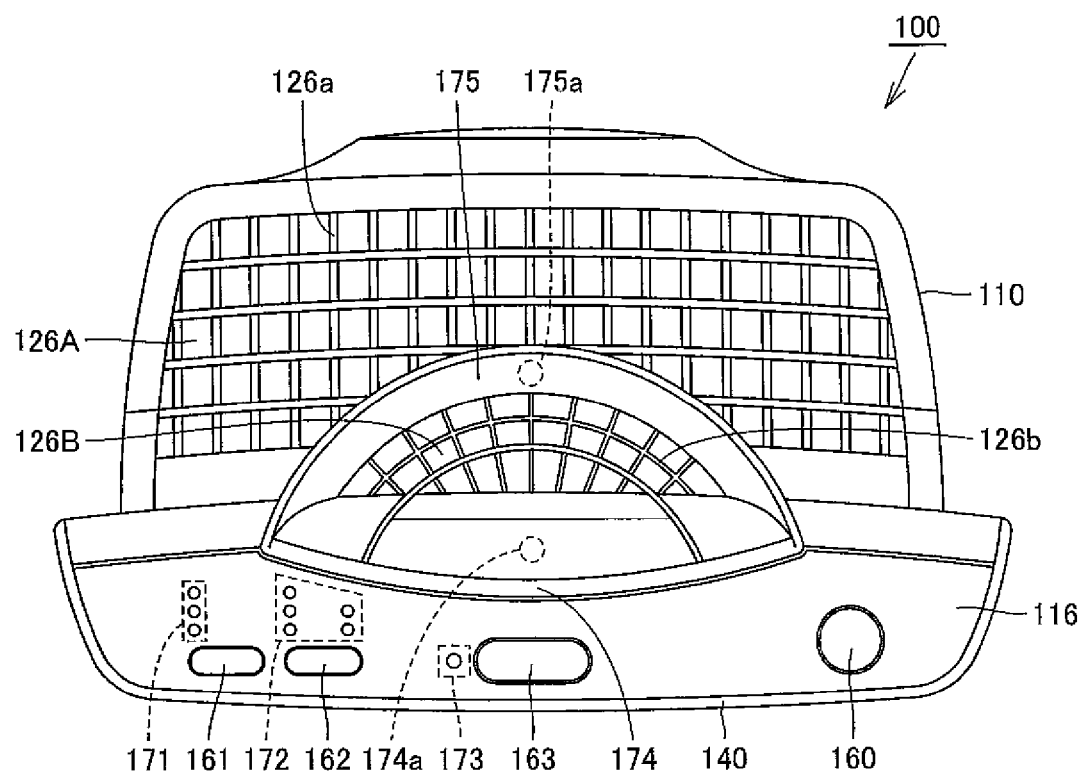
FIG. 3 is a top view of the air cleaner according to the first embodiment of the present invention.
Figure 4:
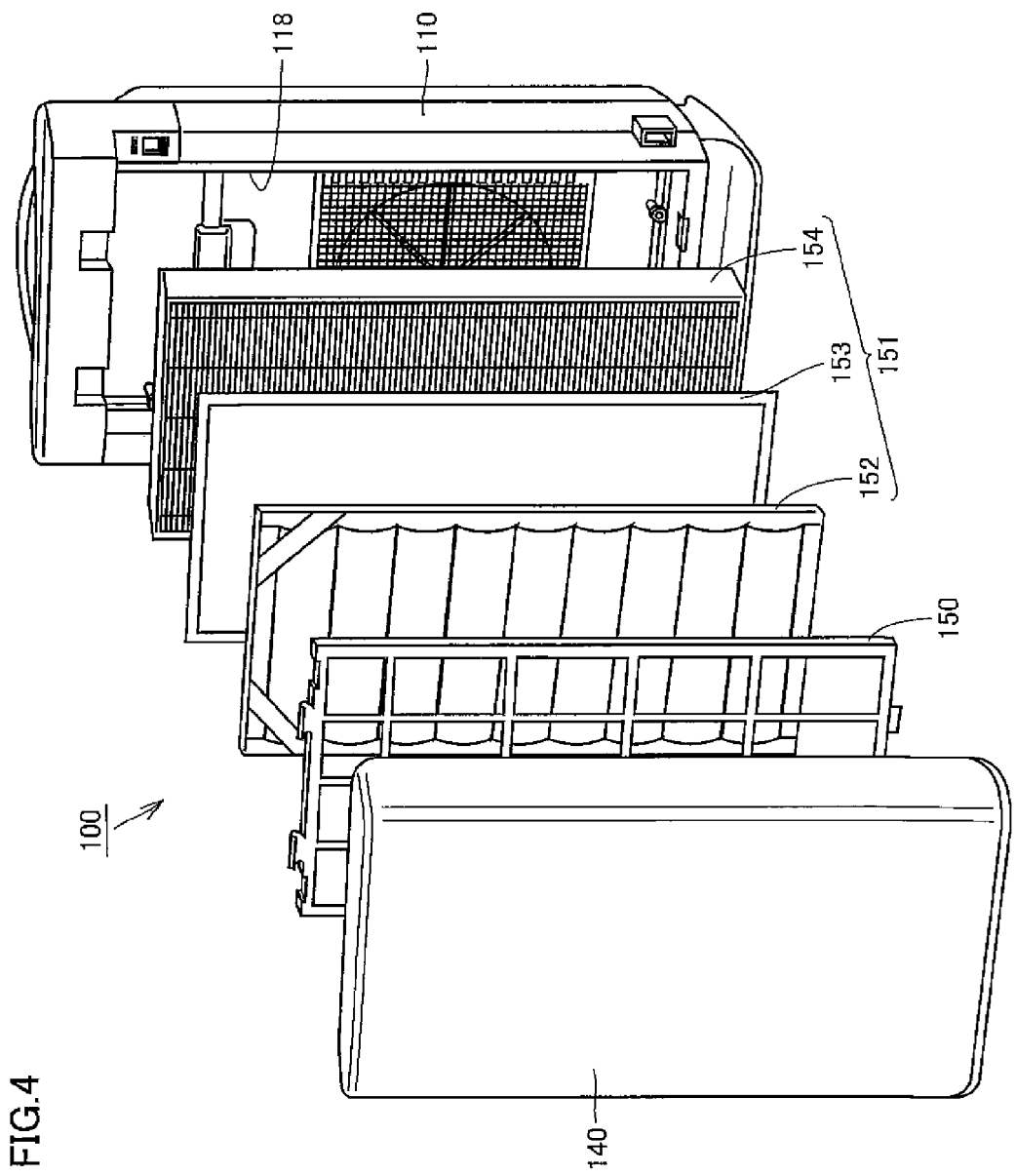
FIG. 4 is an exploded perspective view showing an assembly structure of a front panel, a filter pressing frame, and a filter unit of the air cleaner according to the first embodiment of the present invention.
Figure 5:
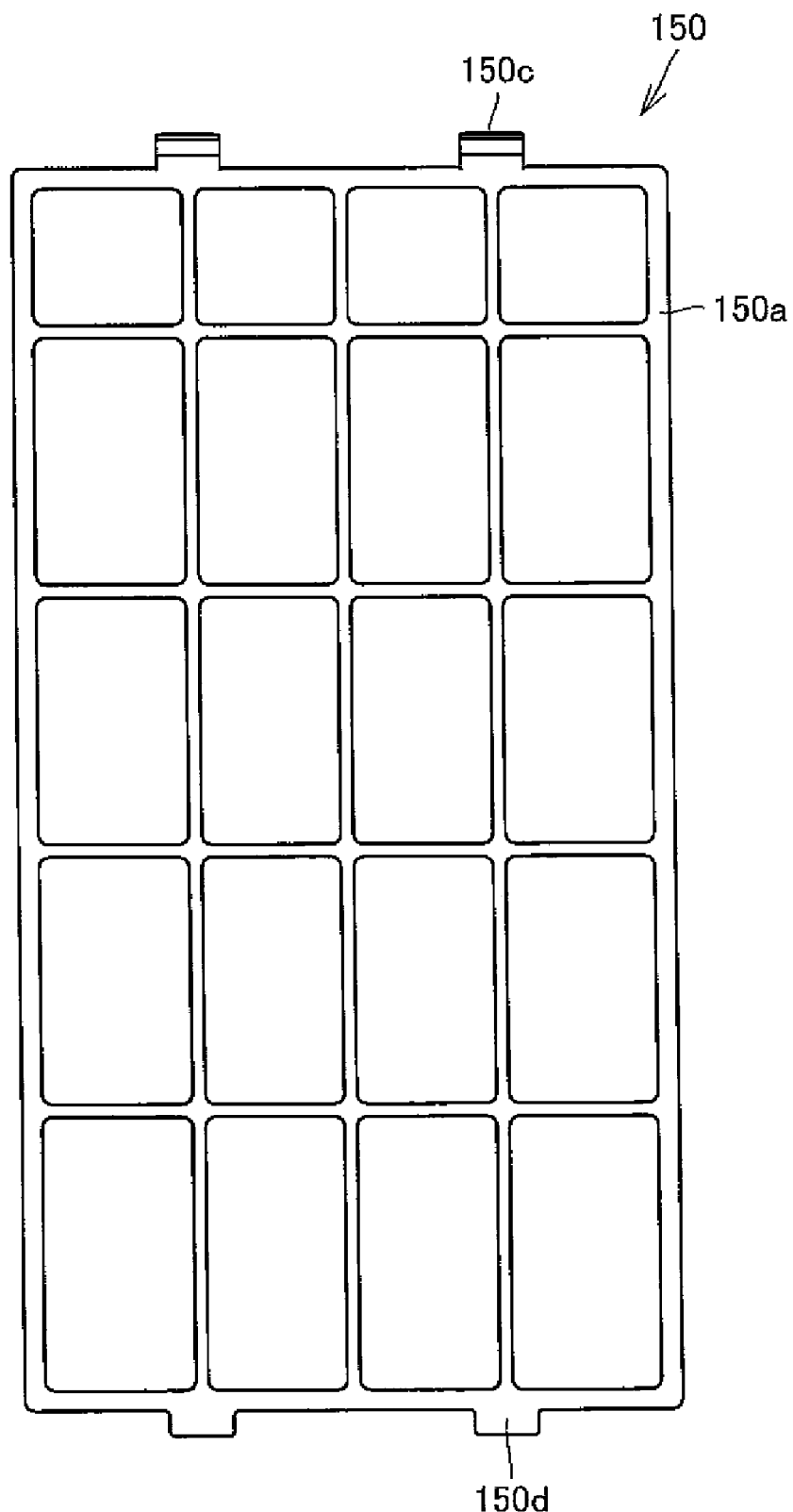
FIG. 5 is a front view of the filter pressing frame.
Figure 6:
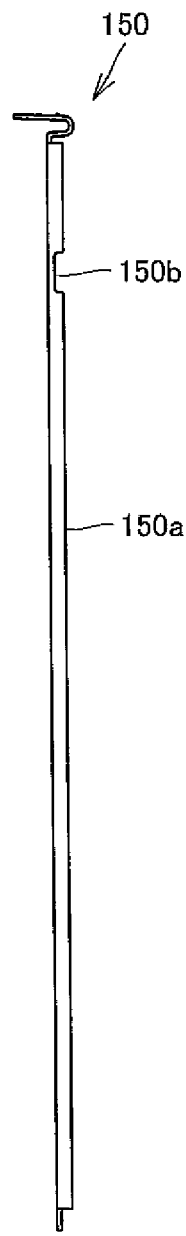
FIG. 6 is a side view of the filter pressing frame.
Figure 7:
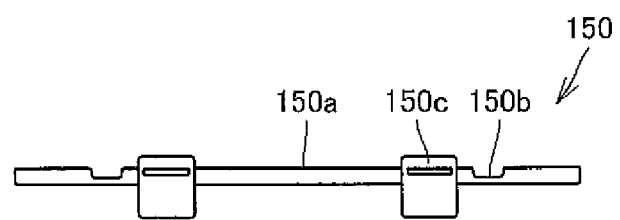
FIG. 7 is a top view of the filter pressing frame.
Figure 8:
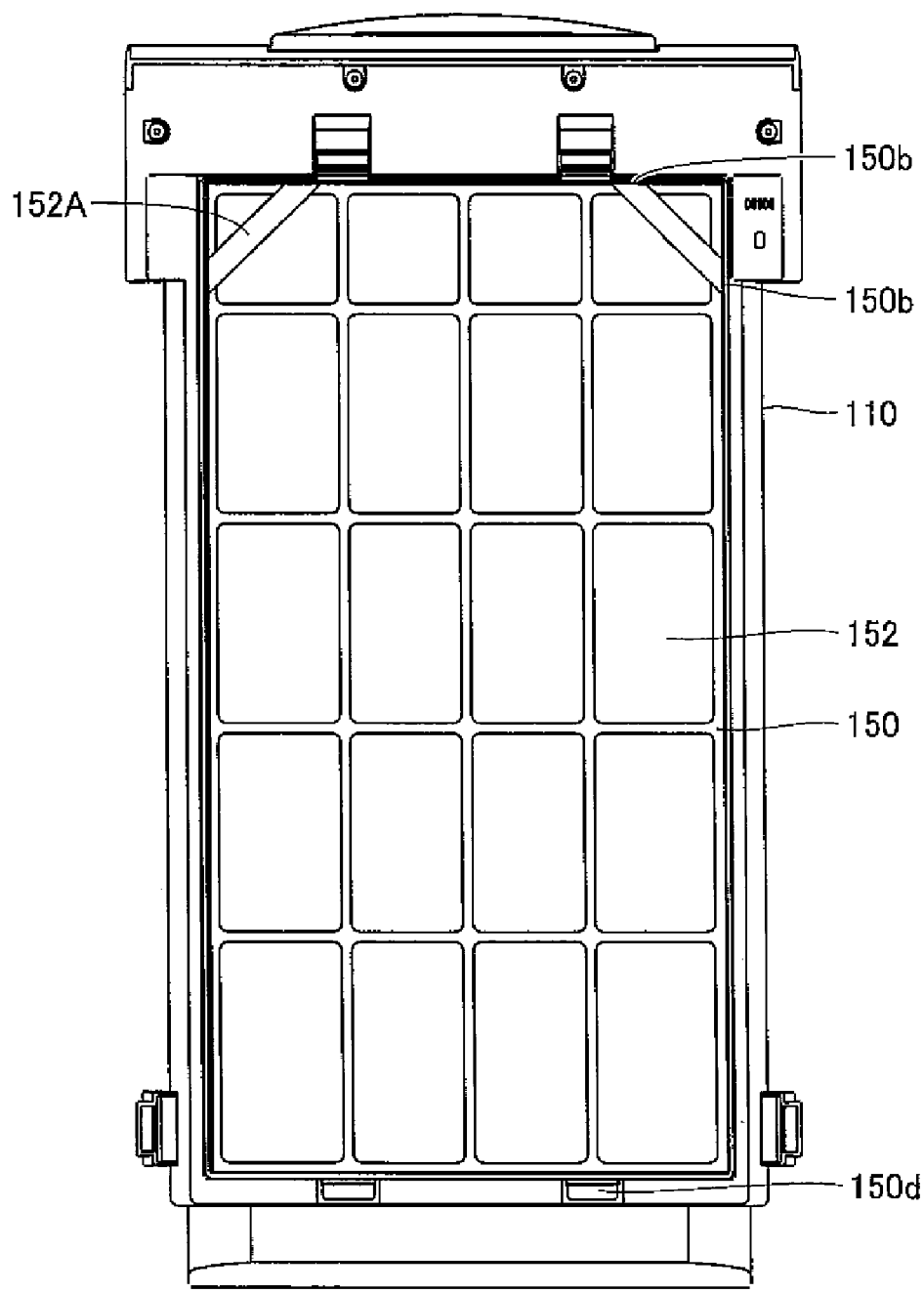
FIG. 8 is a schematic front view showing a state where the filter unit is attached to a main body casing with the filter pressing frame.
Figure 9:
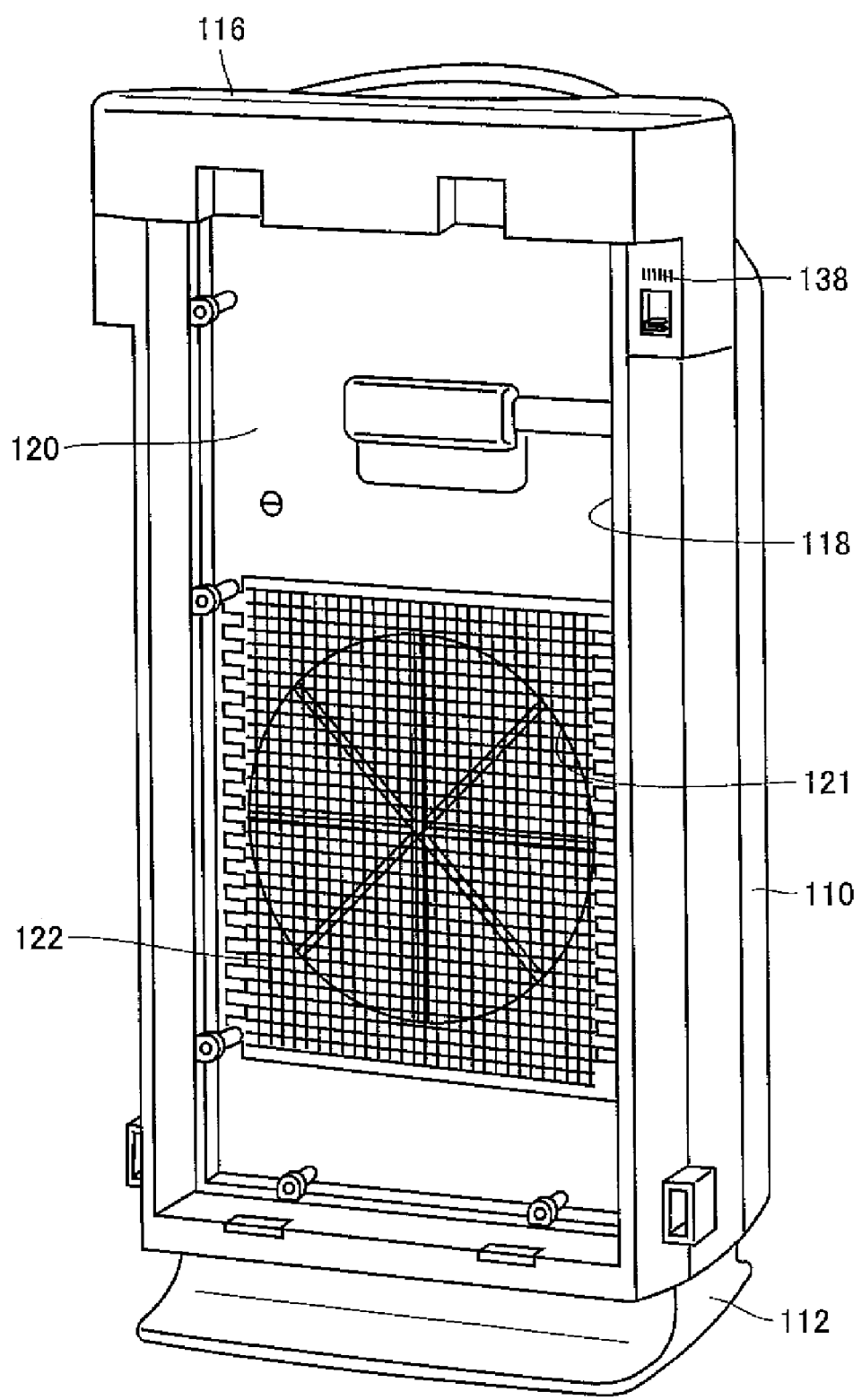
FIG. 9 is a schematic perspective view showing a state where the front panel, the filter pressing frame, and the filter unit are detached from the main body casing in the air cleaner according to the first embodiment of the present invention.

Referring to FIGS. 1 to 9, an external appearance structure of an air cleaner according to a first embodiment of the present invention will be described. FIG. 1 is a schematic perspective view of the air cleaner of the first embodiment when viewed from a front face side. FIG. 2 is a schematic perspective view of the air cleaner when viewed from a rear face side. FIG. 3 is a top view of the air cleaner. FIG. 4 is an exploded perspective view showing an assembly structure of a front panel, a filter pressing frame, and a filter unit of the air cleaner. FIG. 5 is a front view of the filter pressing frame. FIG. 6 is a side view of the filter pressing frame. FIG. 7 is a top view of the filter pressing frame. FIG. 8 is a schematic front view showing a state where the filter unit is attached to a main body casing with the filter pressing frame. FIG. 9 is a schematic perspective view showing a state where the front panel, the filter pressing frame, and the filter unit are detached from the main body casing in the air cleaner of the first embodiment.

As shown in FIGS. 1 to 3, an air cleaner 100 of the first embodiment mainly includes a main body casing 110 and a front panel 140. Main body casing 110 is formed in a rectangular box shape with a front face being opened, and main components of air cleaner 100 are accommodated in main body casing 110. A foot portion 112 is provided below main body casing 110. Foot portion 112 is a part for placing air cleaner 100 on a floor surface or the like in an upright state. An upper panel portion 116 is provided in an upper surface of main body casing 110, and various manipulation buttons, display lamps, and the like are provided in upper panel portion 116. Main body casing 110 is formed by a combination of a plurality of members if needed.

A handgrip portion 114 is provided in a rear face of the main body casing 110. Handgrip portion 114 is provided in consideration of convenience when air cleaner 100 is lifted and conveyed. A power cord 190 is drawn from the rear face of main body casing 110.

Front panel 140 has a side portion 141 vertically provided rearward from the main surface, and side portion 141 is detachably attached to main body casing 110 such that parts of the front face and side face of main body casing 110 are covered with side portion 141. Front panel 140 is attached as a sound insulation material for preventing a noise generated by a sirocco fan or a motor (to be described later) from leaking to the outside of the apparatus during the operation of the apparatus, and front panel 140 ensures beautiful appearance of the apparatus at the same time.

As shown in FIG. 2, a gap is provided between the side face of main body casing 110 and side portion 141 of front panel 140. Gap constitutes an inlet port 124. Inlet port 124 is an opening for introducing the air from the outside into the apparatus. In the side face of main body casing 110, a dust sensor 136 is provided in a portion adjacent to inlet port 124. As shown in FIGS. 2 and 3, air outlets 126A and 126B are provided in an upper portion of main body casing 110. Air outlets 126A and 126B are openings for leading the air purified in the apparatus to the outside of the apparatus.

As described above, the various manipulating buttons and display lamps are provided in upper panel portion 116 of main body casing 110. As shown in FIG. 3, a power button 160 for switching on and off operations of air cleaner 100, an ion generator switching button 161 for switching an operating state of an ion generator, a running mode switching button 162 for switching a running mode of air cleaner 100, an shortcut button 163 for making transfer to a particular running operation with one touch manipulation from a power-off state, and the like are provided in air cleaner 100 of the first embodiment. In addition to these buttons, an ion generator operating state display lamp 171 for indicating a running state of the ion generator, an running mode display lamp 172 for displaying a running mode of air cleaner 100, a shortcut operation display lamp for indicating whether or not running operation of a shortcut button is performed, and the like also are provided in upper panel portion 116.

In air cleaner 100 of the first embodiment, to ensure easy visibility from the front side of air cleaner 100, a pollution state display unit 174 and an ion generator operating state display unit 175 are provided while being integral with air outlet 126B projected from the upper surface of air cleaner 100. Pollution state display unit 174 visually indicates the degree of pollution of the air in the room to a user by modulating a color or brightness of a light emitting diode 174a. Light emitting diode 174a is a light source provided below pollution state display unit 174. Pollution state display unit 174 is configured such that the display of pollution state display unit 174 is switched according to the degree of pollution of the air detected by dust sensor 136 and an odor sensor 138 (see FIG. 9). On the other hand, ion generator operating state display unit 175 visually indicates a running state of the ion generator to the user by modulating the color or brightness of a light emitting diode 175a provided below ion generator operating state display unit 175. Ion generator operating state display unit 175 is a display unit for exerting the same function as ion generator operating state display lamp 171.

As shown in FIG. 4, a filter unit 151 is stored and disposed in a recess portion 118 provided on the front side of main body casing 110. There are various configurations of filter unit 151. In air cleaner 100 of the first embodiment, three filters of a deodorization filter 152, an organic matter removing filter 153, and an antibacterial/dust filter 154 are sequentially laminated from the front side. A filter pressing frame 150 disposed in front of deodorization filter 152, organic matter removing filter 153, and antibacterial/dust filter 154 is fixed to the front face of main body casing 110, so that deodorization filter 152, organic matter removing filter 153, and antibacterial/dust filter 154 are retained in recess portion 118 of main body casing 110.

In the first embodiment, although the three filters are laminated in filter unit 151, the structure of the three filters is not particularly limited. It is necessary that filter unit 151 include at least one filter. For example, filter unit 151 may include only deodorization filter 152.

In the first embodiment, deodorization filter 152 contains a catalyst for removing carbon monoxide. Specifically, the catalyst used in deodorization filter 152 is produced so as to contain 0.1 to 1% palladium compound as a bearing metal, 4 to 7% copper compound, 0.1 to 2% water, and the rest of porous styrene polymer as a bearing body. The use of the catalyst promotes a reaction of the carbon monoxide in the air into carbon dioxide at room temperature, thereby allowing the carbon monoxide in the air to be removed. G3KK (type number) manufactured by Shin-Mei Denshi is used as the catalyst.

Deodorization filter 152 includes a substance (deodorant) such as activated carbon having the deodorization function, and the deodorization function is exerted by adsorbing an odor component. In the first embodiment, the activated carbon is used as a deodorant of deodorization filter 152. The activated carbon is formed in a granular shape. Coconut husk activated carbon, coal-pitch activated carbon, polyacrylonitrile activated carbon, or cellulose activated carbon is used. An average diameter of thin hole ranges from 10 to 13 angstrom. The activated carbon is not limited to the above shape, kinds, and average diameter of thin hole. For example, the activated carbon may be formed in a fibrous shape.

In the first embodiment, deodorization filter 152 contains the carbon monoxide removing catalyst and the activated carbon, and a soft material is used as an encapsulating member for encapsulating the catalyst and the activated carbon. Therefore, deodorization filter 152 cannot stably be placed only by itself. As described later, in order to attach deodorization filter 152 to filter pressing frame 150, deodorization filter 152 includes two filter attaching belts 152A for connecting an upper end of deodorization filter 152 and the side wall (see FIG. 8). On the other hand, because the encapsulating member is used in deodorization filter 152, deodorization filter 152 can be reuse by cleaning deodorization filter 152 with a washing machine. Therefore, in a case where deodorization capability is decreased due to the long-term use, deodorization filter 152 is rolled up and tied with a string, and deodorization filter 152 is taken in the washing machine, so that deodorization filter 152 can easily be washed.

In the first embodiment, one formaldehyde removing filter is included as organic matter removing filter 153. The formaldehyde (HCHO) removing filter contains ethylene urea ($C_2(NH)_2CO$). A chemical reaction is generated as shown in Chemical Formula 1 by containing the ethylene urea. The formaldehyde in the air can be removed by the mechanism shown in Chemical Formula 1.

Chemical Formula 1

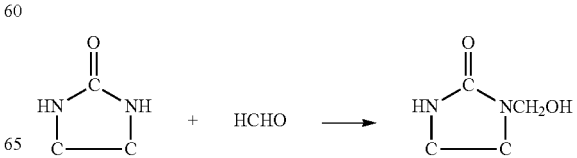

In the first embodiment, an HEPA (High Efficiency Particulate Air) filter is used as antibacterial/dust filter 154. In the HEPA filter, melt-blow nonwoven fabric to which an electromagnet process is performed is mixed in an aggregate including polyester/vinylon nonwoven fabric to form a filtering material, the filtering material is folded, antibacterial sheets made of nonwoven fabric to which a hydroxyapatite process is performed are thermally bonded to upper and lower surfaces of the folded filtering material, and a frame made of nonwoven fabric to which a hot-melt process is performed is melt-bonded thereto. The HEPA filter traps fine dust.

The melt-blow nonwoven fabric is made of fabric obtained by combining relatively-thin fabric having a diameter of about 1 μm and relatively-thick fabric having a diameter of about 3 μm. Therefore, when compared with the conventional technique, pressure loss of antibacterial/dust filter 154 is reduced, and a volume of antibacterial/dust filter 154 can be decreased by about 35%.

Because the antibacterial function is also added to the HEPA filter, the HEPA filter can suppress the growth of the bacteria adhering to the HEPA filter.

As shown in FIGS. 5 and 7, a filter pressing frame 150 includes a frame body 150a, a cut-in portion 150b, a hook portion 150c, and an insertion portion 150d. Frame body 150a is formed in a rectangle shape when viewed from the front face, and includes members for connecting facing sides at several points such that rectangular hollow portions are formed therein. In the first embodiment, frame body 150a includes a hollow frame for forming the hollow portions in five columns and four rows. The air can be sucked in the hollow portions. Four cut-in portions 150b are formed in total, namely, two cut-in portions 150b are formed near corners of the upper-end side in an outer periphery of frame body 150a and two cut-in portions 150b are formed near the corners of the sides connected to the upper-end side. Cut-in portions 150b are formed in a shape of a cut having an approximate depth for retaining a filter attaching belt 152A provided in deodorization filter 152.

Hook portions 150c are connected to the upper-end side of frame body 150a at two points, and hook portions 150c are formed to be able to be hooked when filter unit 151 is fixed to the front face of main body casing 110. Insertion portions 150d are connected to the lower-end side of frame body 150a at two points, and insertion portions 150d are formed to be able to be inserted when filter unit 151 is fixed to the front face of main body casing 110.

As shown in FIG. 8, in order to fix filter unit 151 to main body casing 110, filter attaching belts 152A included in deodorization filter 152 are fitted in cut-in portions 150b provided in filter pressing frame 150 respectively, whereby fixing deodorization filter 152 is fixed to filter pressing frame 150. Then, filter pressing frame 150 and filter unit 151 are disposed in front of main body casing 110. Thereafter, hook portions 150c and insertion portions 150d are fitted in predetermined positions of main body casing 110 respectively, thereby allowing filter unit 151 to be fixed to the front face of main body casing 110 using filter pressing frame 150.

As shown in FIG. 9, a communication hole 121 is made in a partition wall 120 provided at the back of recess portion 118 of main body casing 110, and a metal guard 122 is attached in front of communication hole 121. Partition wall 120 partitions an internal space of main body casing 110 into a front space S1 (see FIG. 10) and a rear space S2 (see FIG. 10), and metal guard 122 is a guard member for preventing a worker from accidentally inserting a finger into an operating fan during a maintenance work. Odor sensor 138 is provided at a predetermined position in the front face of main body casing 110.

Figure 10:
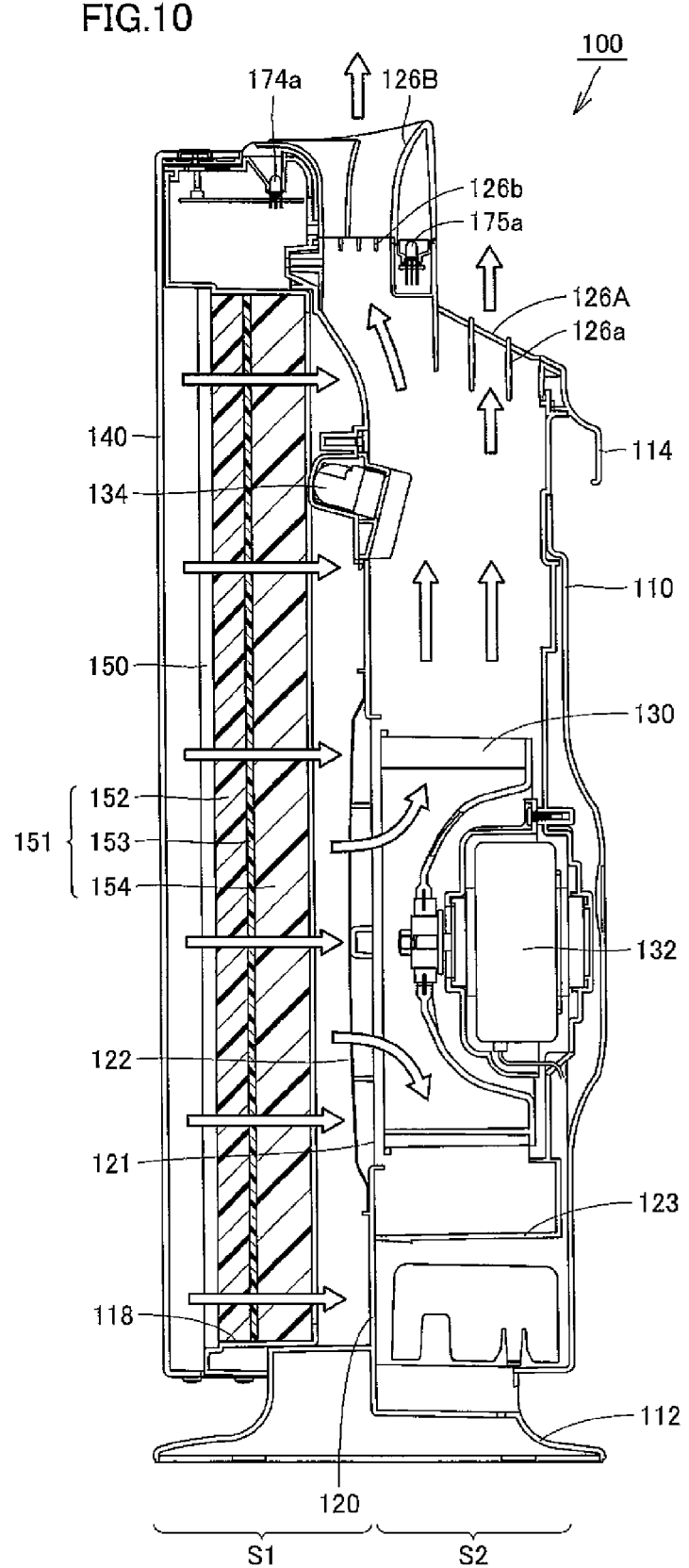
FIG. 10 is a schematic sectional view taken along a line X-X of FIG. 1 of the air cleaner according to the first embodiment of the present invention.
Figure 11:
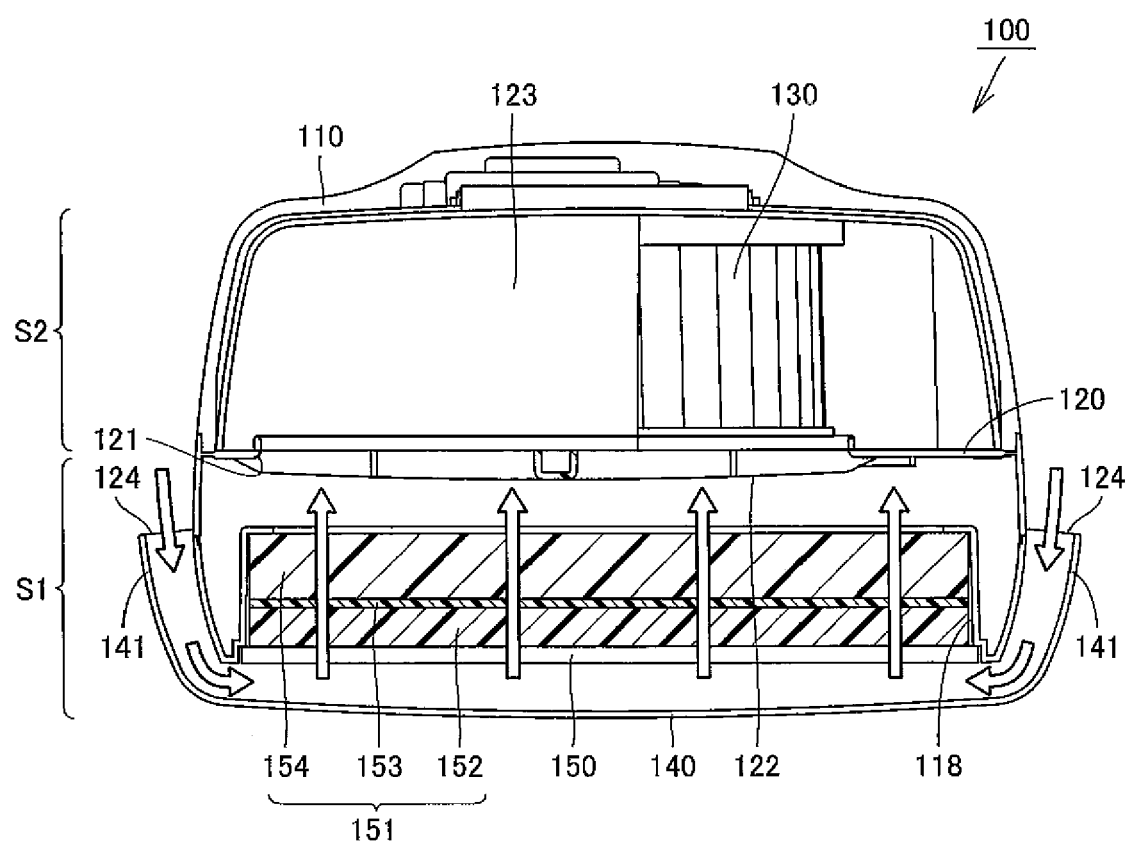
FIG. 11 is a schematic sectional view taken along a line XI-XI of FIG. 1 of the air cleaner according to the first embodiment of the present invention.
Figure 12:
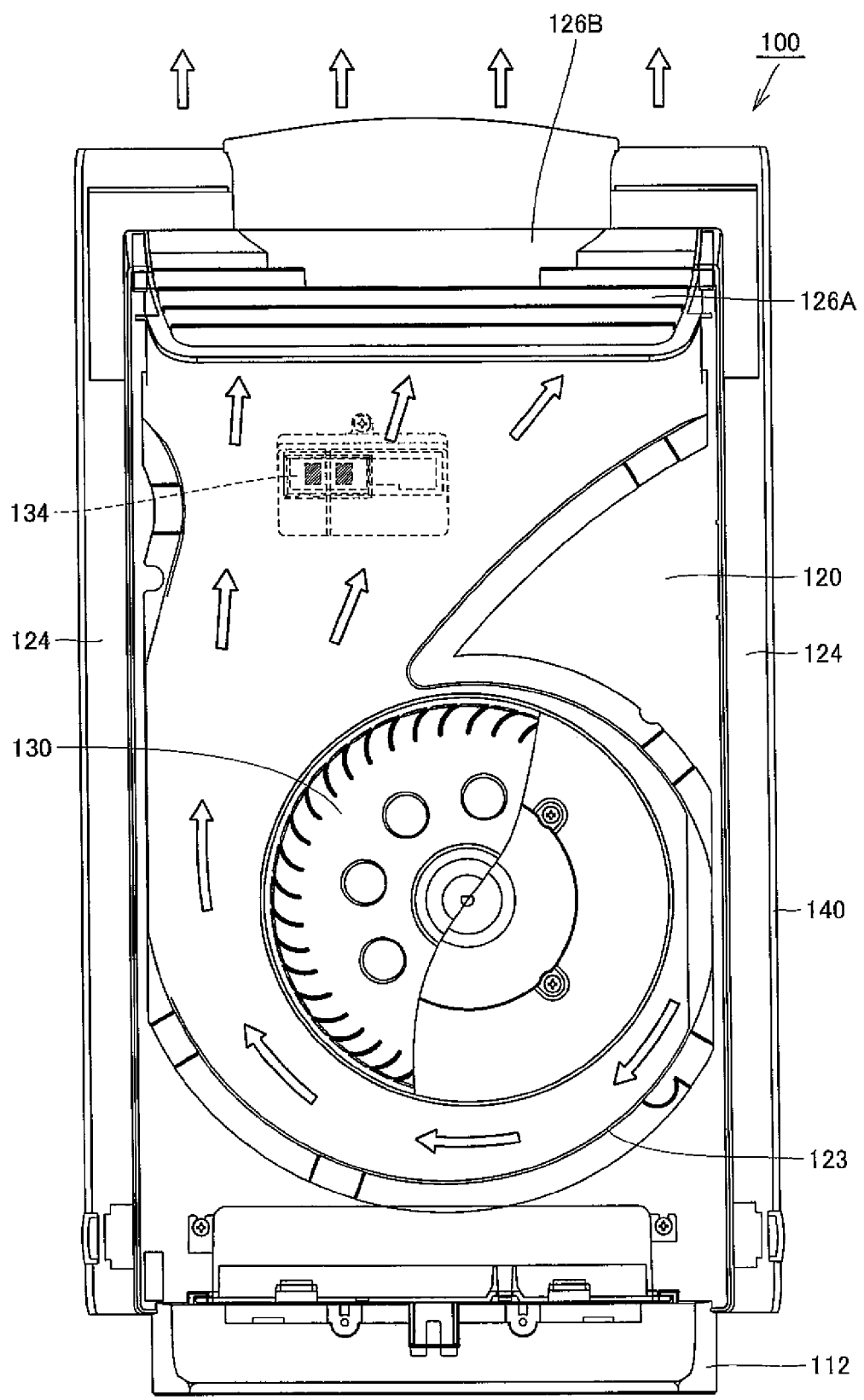
FIG. 12 is a partially broken-out sectional view showing a state where a member constituting a rear portion of the main body casing is detached in the air cleaner according to the first embodiment of the present invention.

Referring to FIGS. 10 to 12, an internal structure of the air cleaner 100 of the first embodiment and an air flow in the apparatus main body will be described below. FIG. 10 is a schematic sectional view taken along a line X-X of FIG. 1 of the air cleaner of the first embodiment. FIG. 11 is a schematic sectional view taken along a line XI-XI of FIG. 1. FIG. 12 is a partially broken-out sectional view showing a state where a member constituting a rear portion of the main body casing is detached in the air cleaner of the first embodiment.

As shown in FIGS. 10 and 11, partition wall 120 is located in air cleaner 100. Filter unit 151 including deodorization filter 152, organic matter removing filter 153, and antibacterial/dust filter 154 are disposed in front of partition wall 120, and front panel 140 is disposed in front of filter unit 151. Filter unit 151 divides front space S1 located between front panel 140 and partition wall 120, and the divided spaces constitute air flow paths respectively. As shown in FIG. 11, front space S1 is communicated with the outside of the apparatus through inlet port 124 in the side of main body casing 110.

As shown in FIGS. 10 to 12, a sirocco fan 130 as a blowing fan is disposed at the back of partition wall 120. Sirocco fan 130 is rotated by a motor 132 disposed at the back of sirocco fan 130. Communication hole 121 in partition wall 120 is made while facing a suction surface of sirocco fan 130.

Rear space S2 of main body casing 110 is communicated with air outlets 126A and 126B provided in the upper portion of main body casing 110. Louver 126a and 126b are provided in air outlet 126A and 126B respectively. Louver 126a and 126b are used to align an orientation of the air blown from air outlet 126A and 126B.

A flow path forming member 123 is disposed in rear space S2 of main body casing 110. Flow path forming member 123 is used to guide the air flow introduced in rear space S2 by sirocco fan 130 to air outlet 126A and 126B, and forms an air flow path in rear space S2 along with partition wall 120. Flow path forming member 123 is formed in a shape to surround sirocco fan 130 in a lower portion thereof and guide the air blown from sirocco fan 130 to air outlet 126A and 126B in an upper portion thereof.

An ion generator 134 is provided at a predetermined position of partition wall 120 facing rear space S2. Ion generator 134 emits at least one of positive ions and negative ions to the air passing through rear space S2. In ion generator 134, oxygen or moisture in the air is ionized by applying an alternating-current voltage between electrodes provided in an ion generating element. An ion emitting surface of ion generator 134 is disposed while facing the air flow path, whereby the generated ions are released to the outside of the apparatus along with of the air flow.

In air cleaner 100 having the above-described configuration, sirocco fan 130 is rotated by motor 132 to generated a negative pressure in front space S1 of main body casing 110, and the air in the room is taken in front space S1 through inlet port 124 laterally located in the main body casing 110 (see FIG. 11). When the air taken in front space S1 passes through filter unit 151, deodorization process and the carbon monoxide removing process, the formaldehyde adsorbing process, the duct trapping process, and the antibacterial process are sequentially performed to the air. Then, the air passes through communication hole 121 made in partition wall 120, and the air is introduced to rear space S2 (see FIGS. 10 and 11).

When the air passes through filter unit 151, filter unit 151 also acts as a prefilter for trapping large dust in the air sucked by sirocco fan 130.

The air flowing in rear space S2 is blown from a peripheral surface portion of sirocco fan 130 toward the outside. The air blown from sirocco fan 130 is guided to flow path forming member 123, the air is raised in rear space S2, and the air is blown out to the room through air outlet 126A and 126B while ion generator 134 adds the positive ions and/or negative ions having a predetermined concentration (see FIGS. 10 and 12). In FIGS. 10 and 12, the air flow is indicated by arrows.

Thus, air cleaner 100 according to the first embodiment of the present invention includes sirocco fan 130 and filter unit 151, and the filter unit 151 includes the filter containing the carbon monoxide removing catalyst. Therefore, the carbon monoxide removing catalyst promotes the reaction of the carbon monoxide in the air into the carbon dioxide, so that the carbon monoxide in the air can be removed.

In the first embodiment, the carbon monoxide removing catalyst can remove the carbon monoxide at room temperature. Therefore, the space where the device for heating the air to a high temperature is not required, so that the air conditioning apparatus having the carbon monoxide removing function can be miniaturized.

Filter unit 151 is thinned by including the carbon monoxide removing catalyst of the first embodiment, so that filter unit 151 can further include one organic matter removing filter 153 for removing the organic matter containing the aldehyde group. Therefore, the organic matter containing the aldehyde group such as the formaldehyde can effectively be removed.

Organic matter removing filter 153 is disposed on the downwind side of deodorization filter 152. Deodorization filter 152 also acts as the prefilter for trapping the large dust in the air. Therefore, organic matter removing filter 153 can more effectively remove the organic matter.

Cut-in portion 150b is provided in a part of filter pressing frame 150. Therefore, during impact or handling, filter attaching belt 152A of deodorization filter 152 can be prevented from disengaging or the deodorization filter 152 can be prevented from falling out. Accordingly, convenience of air cleaner 100 can further be improved.

Second Embodiment

Figure 13:
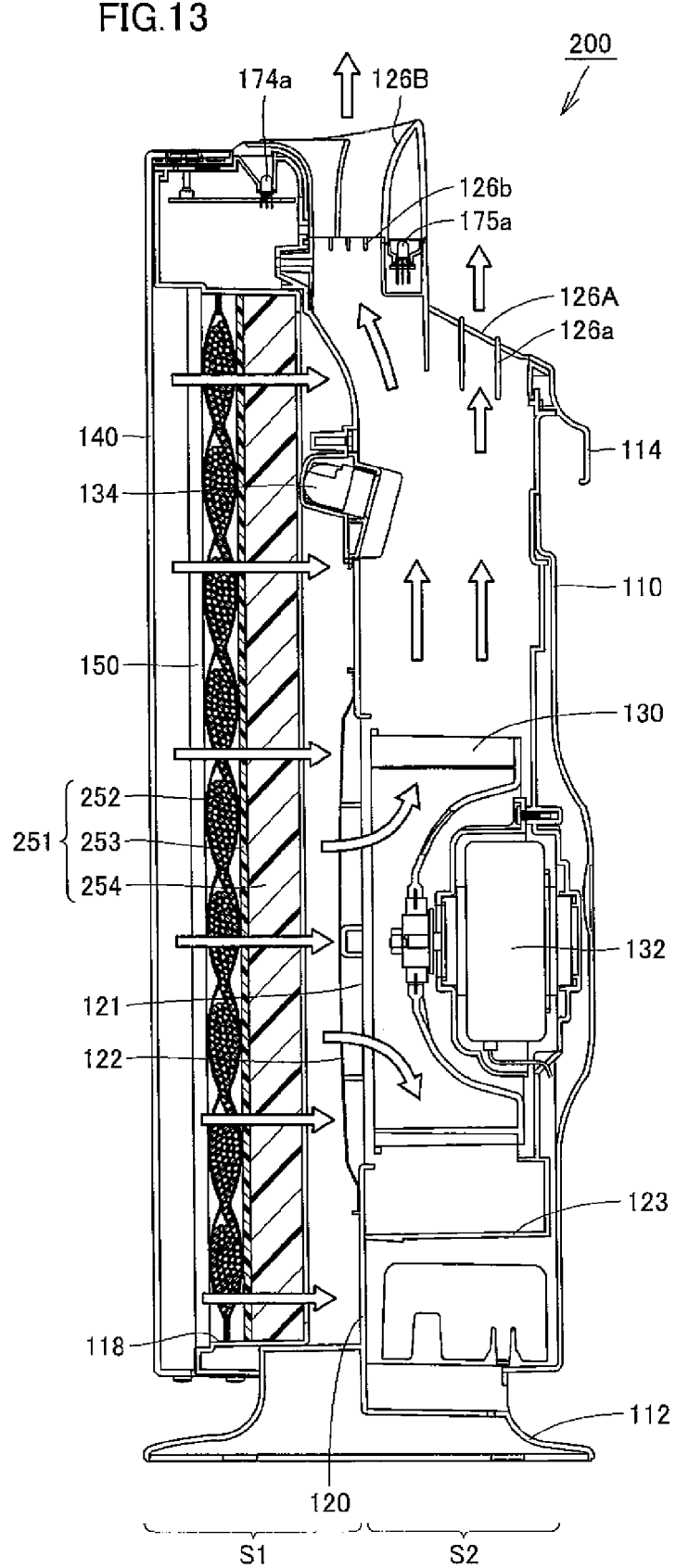
FIG. 13 is a schematic sectional view of an air cleaner according to a second embodiment of the present invention.
Figure 14:
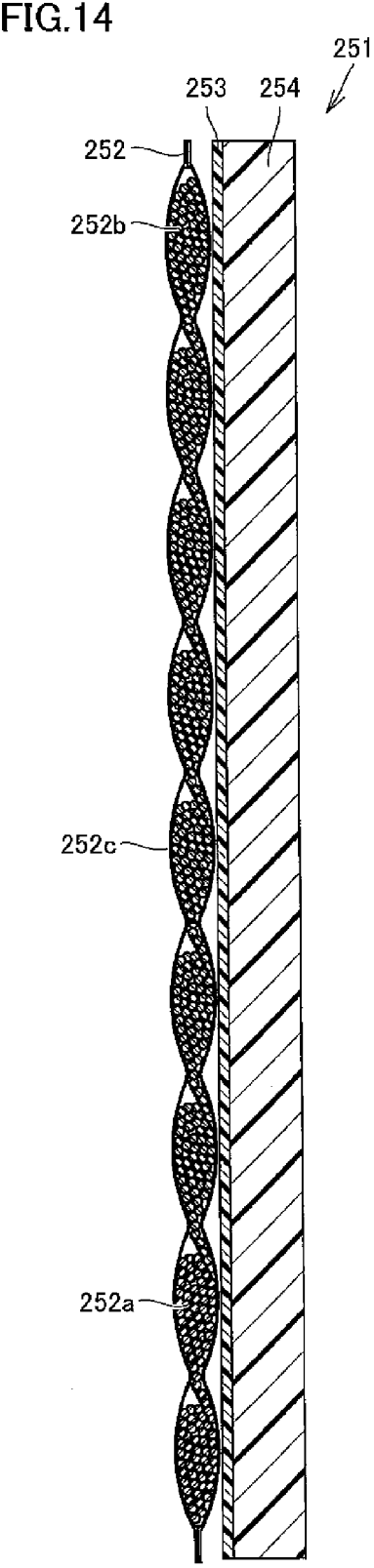
FIG. 14 is a sectional view of a filter unit according to the second embodiment of the present invention.
Figure 15:
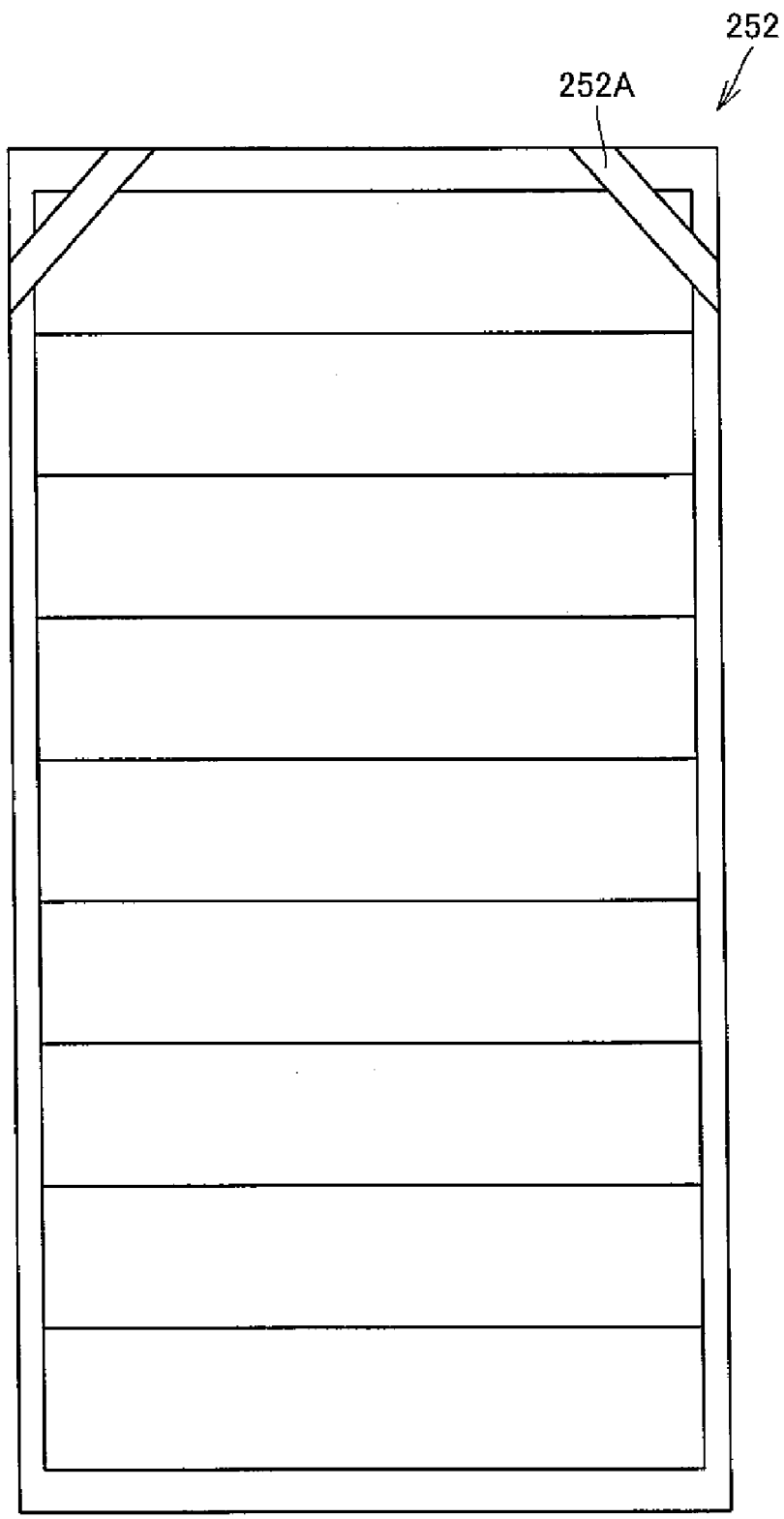
FIG. 15 is a front view of a deodorization filter.
Figure 16:
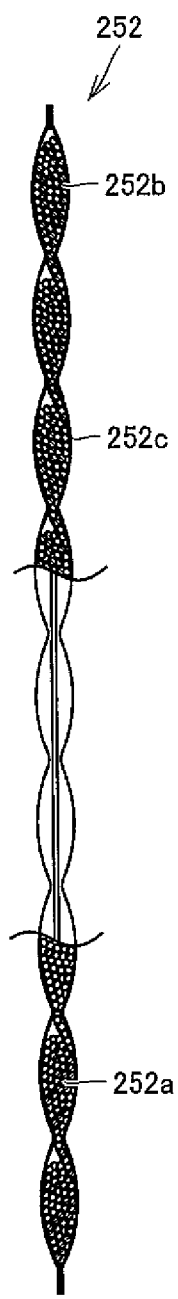
FIG. 16 is a partially broken-out sectional view of the deodorization filter.
Figure 17:
FIG. 17 is a top view of the deodorization filter.

Referring to FIGS. 13 to 17, an air cleaner according to a second embodiment of the present invention will be described. FIG. 13 is a schematic sectional view of an air cleaner of the second embodiment. FIG. 14 is a sectional view of a filter unit of the second embodiment. FIG. 15 is a front view of a deodorization filter. FIG. 16 is a partially broken-out sectional view of the deodorization filter. FIG. 17 is a top view of the deodorization filter.

Referring to FIG. 13, an air cleaner 200 of the second embodiment basically has a configuration similar to the configuration of air cleaner 100 of the first embodiment shown in FIG. 10, and the deodorization filter is illustrated more specifically. The deodorization filter will mainly be described below. A filter unit 251 of the second embodiment includes a deodorization filter 252, an organic matter removing filter 253, and an antibacterial/dust filter 254. Deodorization filter 252 contains a catalyst 252a and a deodorant 252b.

Referring to FIGS. 13 and 14, in deodorization filter 252 of the second embodiment, catalyst 252a for removing the carbon monoxide and deodorant 252b for removing an odor component are contained in one filter. In deodorization filter 252 as the one filter, catalyst 252a is contained in the relatively lower portions, and deodorant 252b is contained in other portions. Specifically, as shown in FIG. 14, in nine bags of deodorization filter 252, catalyst 252a is stored in the lowermost and second-lowermost bags 252c, and deodorant 252b is stored in the remaining seven bags 252c.

Referring to FIGS. 15 and 17, deodorization filter 252 includes a plurality of coupled deodorant storage chambers for storing deodorant 252b and a plurality of coupled catalyst storage chambers for storing catalyst 252a, and deodorization filter 252 is formed in a rectangle when viewed from the front face. Each of the outer shapes of the deodorant storage chambers and catalyst storage chambers is formed in the substantially same bag 252c, and bag 252c is formed by sewing two meshes together. Roughness of the mesh is set to an extent that pieces of the granular catalyst 252a and deodorant 252b do not leak to the outside. Deodorization filter 252 includes spacers 252d having air permeability at upper and lower ends thereof.

The internal structure of air cleaner 200 and the air flow in the apparatus main body of the second embodiment are similar to the internal structure of air cleaner 100 and the air flow in the apparatus main body of the first embodiment, so that the description thereof is not repeated.

Thus, in air cleaner 200 according to the second embodiment of the present invention, deodorization filter 252 contains catalyst 252a and deodorant 252b in the one filter, so that the carbon monoxide and the odor component can be removed by the one filter. Therefore, the filter unit 251 can be thinned.

The, modifications of the second embodiment will be described. FIGS. 18 to 23 are sectional views showing first to sixth modifications of filter unit 251 constituting air cleaner 200 of the second embodiment. Although the configurations of the filter units in the first to sixth modifications have the configurations similar to that of filter unit 251 of the second embodiment, the first to sixth modifications differ from the second embodiment in the configuration of the deodorization filter 252.

Figure 18:
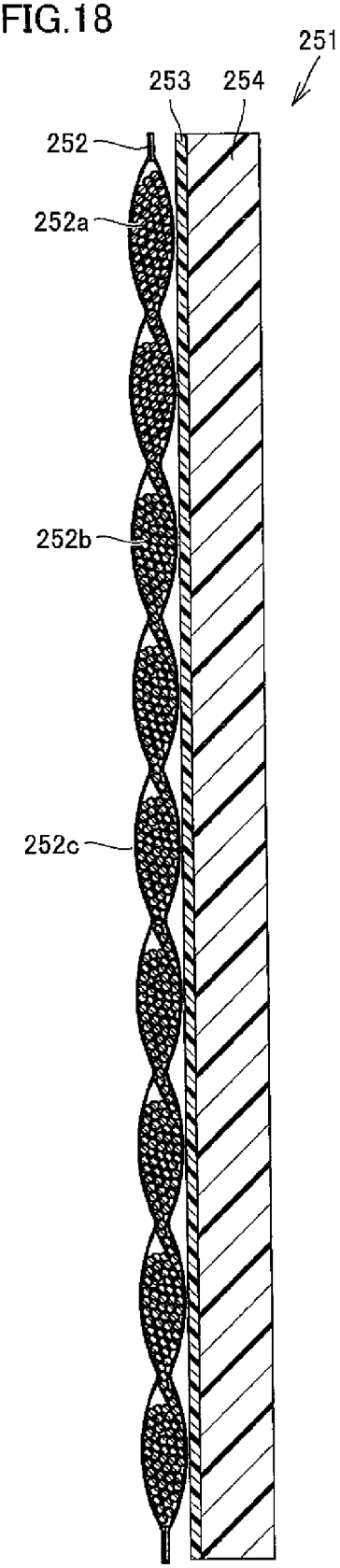
FIG. 18 is a sectional view of a filter unit in a first modification.

FIG. 18 is a sectional view of filter unit 251 in the first modification. Deodorization filter 252 in the first modification is formed by one filter for storing catalyst 252a in the relatively upper portions and deodorant 252b in other portions. Specifically, as shown in FIG. 18, deodorization filter 252 includes the catalyst storage chamber for storing catalyst 252a in the uppermost and second-uppermost bags 252c and the deodorant storage chamber for storing deodorant 252b in the remaining seven bags 252c.

Figure 19:
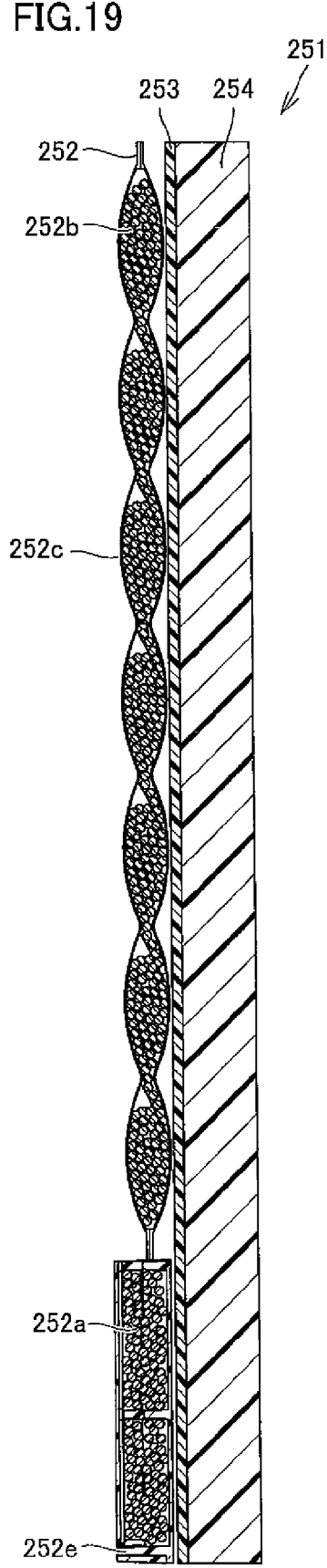
FIG. 19 is a sectional view of a filter unit in a second modification.

FIG. 19 is a sectional view of the filter unit 251 in the second modification. Deodorization filter 252 of the second modification includes bags 252c and another frame material 252e. The bags 252c for storing deodorant 252b are located in the upper portion of deodorization filter 252, and the frame material 252e for storing catalyst 252a is located in the lower portion. Frame material 252e is formed in the stationary shape.

In deodorization filter 252 of the second modification, catalyst 252a is stored in the member different from deodorant 252b. Therefore, because the deodorant storage chamber for storing deodorant 252b can be washed with the washing machine, the convenience is enhanced when only deodorant 252b is reused.

Figure 20:
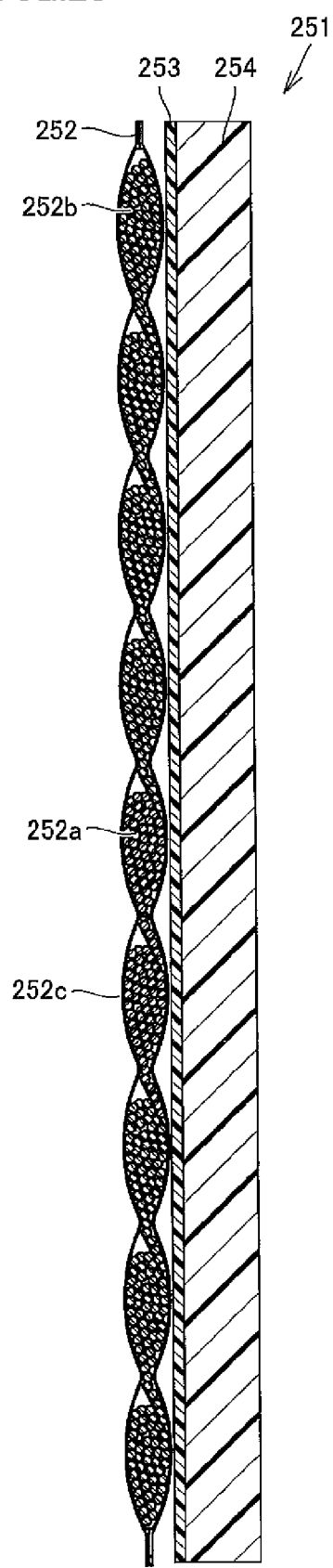
FIG. 20 is a sectional view of a filter unit in a third modification.

FIG. 20 is a sectional view of the filter unit 251 in the third modification. In deodorization filter 252 of the third modification, the catalyst storage chamber for storing catalyst 252a is disposed in the substantial center of deodorization filter 252 when deodorization filter 252 is attached to main body casing 110. Specifically, as shown in FIG. 20, in nine bags 252c of deodorization filter 252, the catalyst storage chambers are located in fourth and fifth lowermost bags 252c, and the deodorant storage chambers are located in remaining bags 252c.

Figure 21:
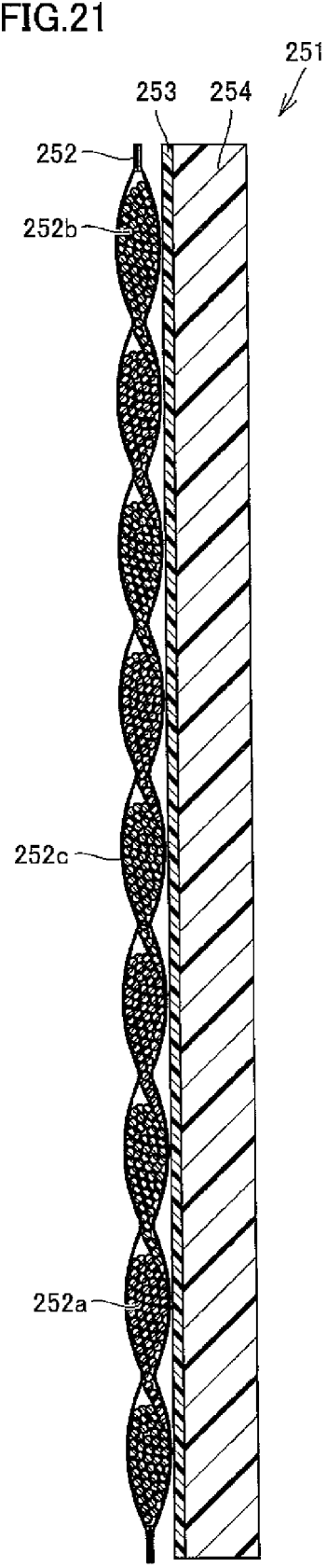
FIG. 21 is a sectional view of a filter unit in a fourth modification.

FIG. 21 is a sectional view of the filter unit 251 in the fourth modification. In the deodorization filter of the fourth modification, the deodorant storage chambers and the catalyst storage chambers are alternatively disposed. Specifically, as shown in FIG. 21, in nine bags 252c, the deodorant storage chambers and the catalyst storage chambers are alternately disposed from the bottom, and the deodorant storage chamber is disposed in upper-end bag 252c.

Figure 22:
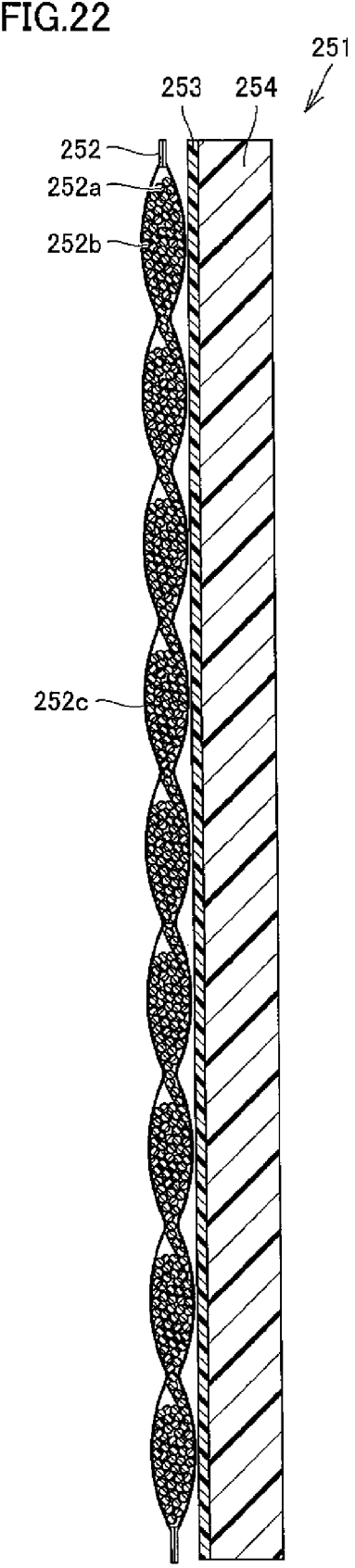
FIG. 22 is a sectional view of a filter unit in a fifth modification.

FIG. 22 is a sectional view of the filter unit 251 in the fifth modification. As shown in FIG. 22, in deodorization filter of the fifth modification, catalyst 252a is mixed in deodorant 252b.

Figure 23:
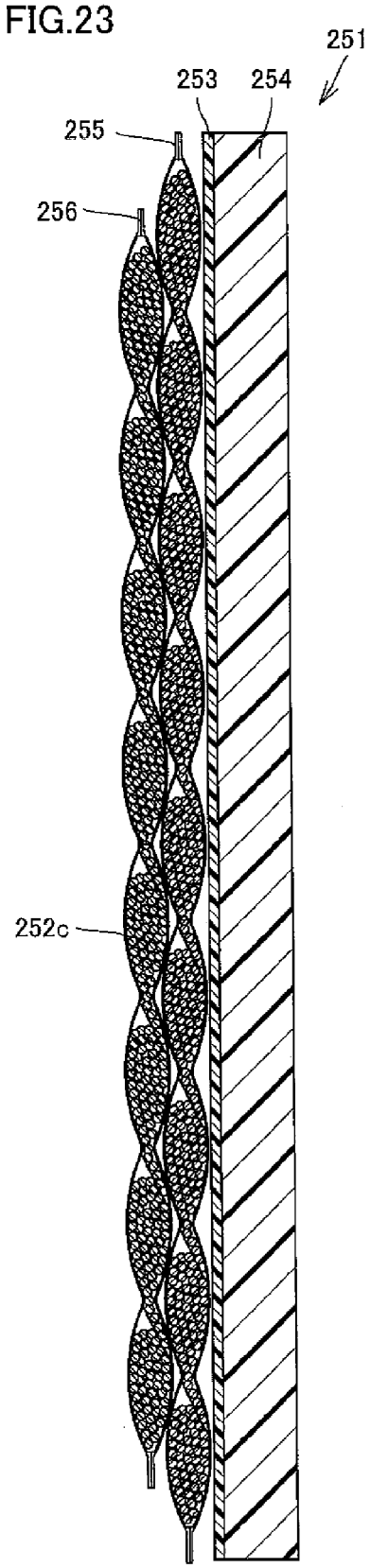
FIG. 23 is a sectional view of a filter unit in a sixth modification.

FIG. 23 is a sectional view of the filter unit 251 in the sixth modification. Filter unit of the sixth modification includes one catalyst filter 255 containing the catalyst and one deodorization filter 256 containing the deodorant. Specifically, as shown in FIG. 23, coupling portions of the deodorant storage chambers of deodorization filter 256 are disposed so as to overlap the substantial center portions of the catalyst storage chambers of catalyst filter 255.

In the filter unit of the sixth modification, because deodorization filter 255 can also act as the prefilter, catalyst filter 255 is disposed on the downwind side of deodorization filter 256.

Thus, in the filter units 251 of the first to fifth modifications, deodorization filter 252 contains catalyst 252a and deodorant 252b in the one filter, so that the carbon monoxide and the odor component can be removed by the one filter. Therefore, filter unit 251 can be thinned.

Filter unit 251 of the sixth modification contains the further amounts of catalyst and deodorant, so that the further amounts of carbon monoxide and odor component in the air can be removed. The space portions of the catalyst storage chamber and deodorant storage chamber do not overlap with each other, so that filter unit 251 can be thinned.

Third Embodiment

Figure 24:
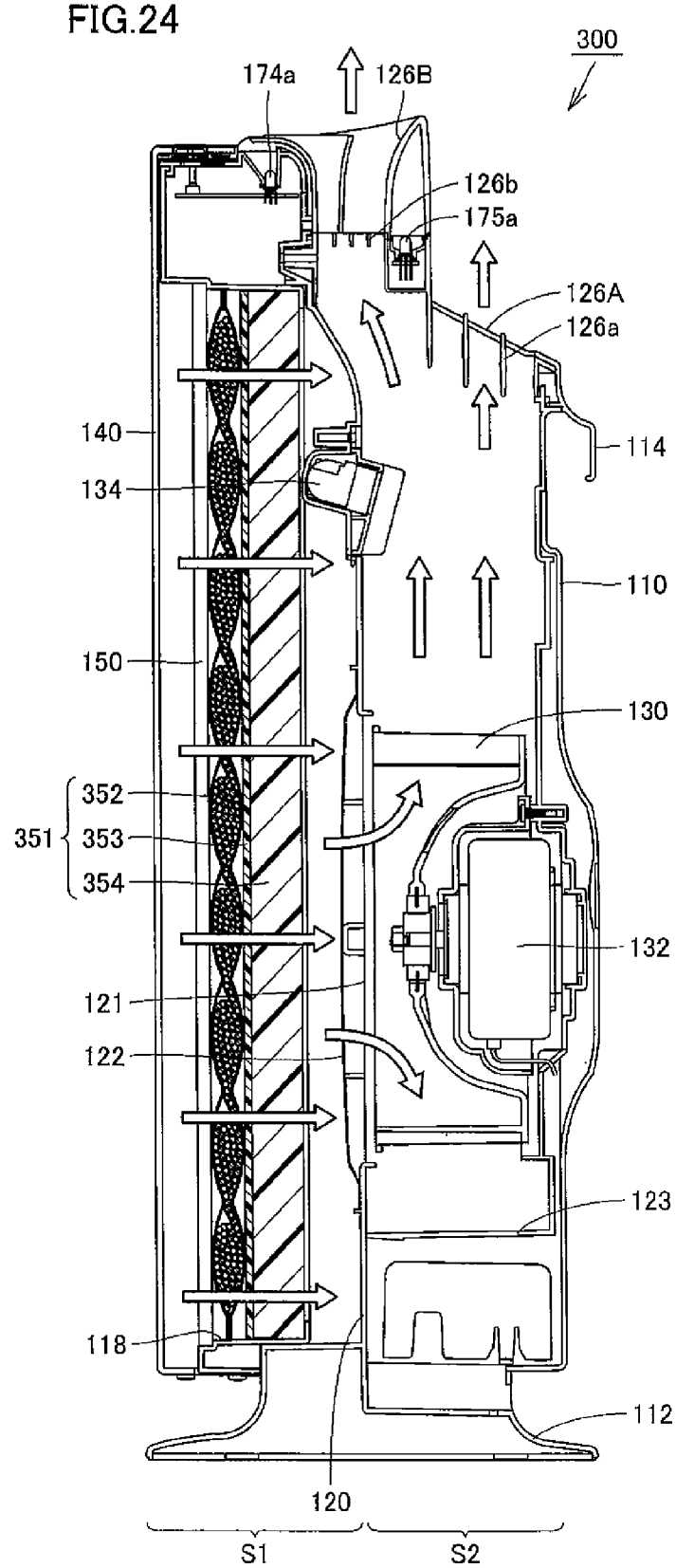
FIG. 24 is a schematic sectional view of an air cleaner according to a third embodiment of the present invention.
Figure 25:
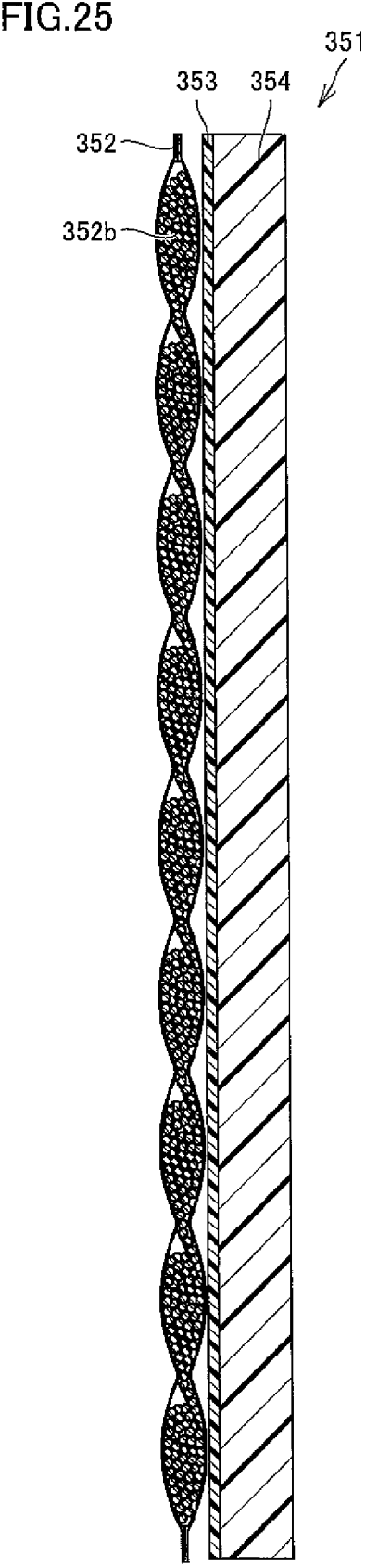
FIG. 25 is a sectional view of a filter unit in the third embodiment of the present invention.

Referring to FIGS. 24 and 25, an air cleaner according to a third embodiment of the present invention will be described. FIG. 24 is a schematic sectional view of an air cleaner of the third embodiment. FIG. 25 is a sectional view of a filter unit in the third embodiment of the present invention.

Referring to FIG. 24, although an air cleaner 300 of the third embodiment basically has a configuration similar to the configuration of air cleaner 100 of the first embodiment shown in FIG. 10, a filter unit of the third embodiment differs from the filter unit 151 of FIG. 10 in the configuration.

As shown in FIG. 25, a filter unit 351 included in air cleaner 300 of the third embodiment includes one deodorization filter 352 for removing the odor component and one organic matter removing filter 353 for removing the organic matter containing the aldehyde group. Particularly, filter unit 351 includes a deodorization filter 352, an organic matter removing filter 353, and an antibacterial/dust filter 354.

Deodorization filter 352 contains only a substance (deodorant 352b) such as activated carbon having the deodorization function, and exerts the deodorization function by adsorbing the odor component. In the third embodiment, similarly to the first embodiment, activated carbon is used as the deodorant.

Organic matter removing filter 353 is formed in a formaldehyde removing filter.

In the third embodiment, the formaldehyde removing filter similar to the first embodiment is used.

In the third embodiment, the HEPA filter similar to the first embodiment is used as antibacterial/dust filter 354.

Referring to FIGS. 24 and 25, organic matter removing filter 353 is disposed on the downwind side of deodorization filter 352. Particularly, the three filters of deodorization filter 352, organic matter removing filter 353, and antibacterial/dust filter 354 are laminated from the windward side in the air flowing direction.

The internal structure of air cleaner 300 and the air flow in the apparatus main body of the third embodiment are similar to the internal structure of air cleaner 100 and the air flow in the apparatus main body of the first embodiment, so that description thereof is not repeated.

Thus, in air cleaner 300 of the third embodiment, filter unit 351 includes one deodorization filter 352 for removing the odor component and one organic matter removing filter 353 for removing the organic matter containing the aldehyde group, so that the organic matter containing the aldehyde group can effectively be removed.

In a case where only the function of organic matter removing filter 353 is decreased, only organic matter removing filter 353 can be replaced without replacing other members. Therefore, the convenience is enhanced in air cleaner 300 because the filters can be replaced according to the use environment of air cleaner 300.

Organic matter removing filter 353 is disposed on the downwind side of deodorization filter 352. In filter unit 351, deodorization filter 352 also acts as the prefilter for trapping the large dust in the air sucked by sirocco fan 130. Therefore, organic matter removing filter 353 can more effectively remove the organic matter.

In the descriptions of the first to third embodiments, the floor-mounted air cleaner is illustrated as the air conditioning apparatus. However, the present invention is not limited to the floor-mounted air cleaner. The air conditioning apparatus of the present invention shall includes a general apparatus for introducing the air from the outside of the apparatus to the inside and delivering the air to the outside of the apparatus after a certain process is performed to the introduced air. Accordingly, in addition to the floor-mounted air cleaner, the air conditioning apparatus shall include a wall-hung air cleaner, a built-in air cleaner, an in-car air cleaner, an air harmonic generator, a dehumidifier, a humidifier, an electric heater, an oil stove, an oil fan heater, a gas heater, a refrigerator, a cooler box, an air conditioning duct for building, and an in-car air conditioning duct.

The above-disclosed embodiments are illustrative in every point, and are not limitative. The technical scope of the present invention is defined by the appended claims, and includes all the modifications equivalent to the meaning and within the scope of the claims.

The invention claimed is:

1. An air conditioning apparatus comprising:
   a filter including an air cleaning catalyst and a deodorant; and
   a blowing fan for causing an air flow to pass through said filter,
   wherein said air cleaning catalyst and said deodorant of said filter are separately stored and disposed in parallel in air passages, respectively, and
   wherein said deodorant is disposed only in a region facing a blade region of said blowing fan and said air cleaning catalyst is disposed only in a region facing a peripheral region of a blade of said blowing fan.

2. The air conditioning apparatus according to claim 1, wherein the region having said deodorant disposed therein and facing the blade region of said blowing fan is greater in air volume than the region having said air cleaning catalyst disposed therein and facing the peripheral region of the blade of said blowing fan.

3. The air conditioning apparatus according to claim 1, wherein the region having said deodorant disposed therein and facing the blade region of said blowing fan is positioned in a central portion and the region having said air cleaning catalyst disposed therein and facing the peripheral region of the blade of said blowing fan is positioned in a peripheral portion.

4. The air conditioning apparatus according to claim 1, wherein the region having said deodorant disposed therein and facing the blade region of said blowing fan is subjected to higher air flow velocity than the region having said air cleaning catalyst disposed therein and facing the peripheral region of the blade of said blowing fan.

5. The air conditioning apparatus according to claim 1, wherein the region having said deodorant disposed therein and facing the blade region of said blowing fan is lower in reaction rate than the region having said air cleaning catalyst disposed therein and facing the peripheral region of the blade of said blowing fan.

6. The air conditioning apparatus according to claim 1, wherein the region having said deodorant disposed therein is greater in volume than the region having said air cleaning catalyst disposed therein.

7. A filter unit including an air cleaning filter detachably attached to an air conditioning apparatus, wherein
said air cleaning filter is formed by integrating regions having an air cleaning catalyst and a deodorant, respectively, separately stored therein, and,
when said filter unit is attached to said air conditioning apparatus, the region having said deodorant stored therein is disposed only in a region facing a blade region of a blowing fan of said air conditioning apparatus and the region having said air cleaning catalyst stored therein is disposed only in a region facing a peripheral region of a blade of the blowing fan of said air conditioning apparatus.

8. The filter unit according to claim 7, wherein the regions having said air cleaning catalyst and said deodorant, respectively, separately stored therein are disposed in parallel in air passages, respectively, formed in said air conditioning apparatus.

* * * * *